US00PP31584P2

(12) United States Plant Patent
Misato

(10) Patent No.: US PP31,584 P2
(45) Date of Patent: Mar. 24, 2020

(54) ***MANDEVILLA* PLANT NAMED 'SUNPA 127'**

(50) Latin Name: *Mandevilla hybrida*
Varietal Denomination: Sunpa 127

(71) Applicant: Tomoya Misato, Shiga (JP)

(72) Inventor: Tomoya Misato, Shiga (JP)

(73) Assignee: Suntory Flowers, Limited, Tokyo (JP)

( * ) Notice: Subject to any disclaimer, the term of this patent is extended or adjusted under 35 U.S.C. 154(b) by 0 days.

(21) Appl. No.: 16/350,644

(22) Filed: Dec. 14, 2018

(51) Int. Cl.
*A01H 5/02* (2018.01)
*A01H 6/08* (2018.01)

(52) U.S. Cl.
USPC ..... Plt./232

(58) Field of Classification Search
USPC ..... Plt./232
See application file for complete search history.

*Primary Examiner* — Susan McCormick Ewoldt
(74) *Attorney, Agent, or Firm* — C. A. Whealy

(57) ABSTRACT

A new and distinct cultivar of *Mandevilla* plant named 'Sunpa 127', characterized by its trailing plant habit; vigorous growth habit; freely branching habit; early and freely flowering habit; long flowering period; and medium-sized white-colored flowers with yellow orange-colored throats.

1 Drawing Sheet

Botanical designation: *Mandevilla hybrida.*
Cultivar denomination: 'SUNPA 127'.

BACKGROUND OF THE INVENTION

The present invention relates to a new and distinct cultivar of *Mandevilla* plant, botanically known as *Mandevilla hybrida* and hereinafter referred to by the name 'Sunpa 127'.

The new *Mandevilla* plant is a product of a planned breeding program conducted by the Inventor in Higashiomi, Shiga, Japan. The objective of the breeding program is to create new trailing and freely branching *Mandevilla* plants with freely flowering habit and attractive flowers.

The new *Mandevilla* plant originated from a cross-pollination in Higashiomi, Shiga, Japan in May, 2010 of a proprietary selection of *Mandevilla hybrida* identified as code number 02MH11-4, not patented, as the female, or seed parent with a proprietary selection of *Mandevilla hybrida* identified as code number MH-58, not patented, as the male, or pollen, parent. The new *Mandevilla* plant was discovered and selected by the Inventor as a single flowering plant from within the progeny of the stated cross-pollination in a controlled greenhouse environment in Higashiomi, Shiga, Japan in September, 2011.

Asexual reproduction of the new *Mandevilla* plant by terminal vegetative cuttings in Higashiomi, Shiga, Japan since March, 2012 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunpa 127'. These characteristics in combination distinguish 'Sunpa 127' as a new and distinct *Mandevilla* plant:

1. Trailing plant habit.
2. Vigorous growth habit.
3. Freely branching habit.
4. Early and freely flowering habit.
5. Long flowering period.
6. Medium-sized white-colored flowers with yellow orange-colored throats.

Plants of the new *Mandevilla* can be compared to plants of the female parent selection. Plants of the new *Mandevilla* differ primarily from plants of the female parent selection in flower color as plants of the new *Mandevilla* have white-colored flowers whereas plants of the female parent selection have red-colored flowers.

Plants of the new *Mandevilla* can be compared to plants of the male parent selection. Plants of the new *Mandevilla* differ primarily from plants of the male parent selection in plant habit as plants of the new *Mandevilla* have a trailing plant habit whereas plants of the male parent selection have a semi-upright plant habit.

Plants of the new *Mandevilla* can be compared to plants of the *Mandevilla amabilis* X *Mandevilla boliviensis* 'Sunmandeho', disclosed in U.S. Plant Pat. No. 11,556. In side-by-side comparisons, plants of the new *Mandevilla* differ from plants of 'Sunmandeho' in the following characteristics:

1. Plants of the new *Mandevilla* are more trailing than and not as upright as plants of 'Sunmandeho'.
2. Plants of the new *Mandevilla* have shorter internodes than plants of 'Sunmandeho'.
3. Plants of the new *Mandevilla* have smaller and darker green-colored leaves than plants of 'Sunmandeho'.
4. Plants of the new *Mandevilla* have smaller flowers than plants of 'Sunmandeho'.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph at the top of the sheet comprises a side perspective view of a typical flowering plant of 'Sunpa 127' grown in a container.

The photograph at the bottom of the sheet is a close-up view of a typical flower of 'Sunpa 127'.

DETAILED BOTANICAL DESCRIPTION

The aforementioned photographs and following observations, measurements and values describe plants grown during the summer in 15-cm containers in an outdoor nursery in Higashiomi, Shiga, Japan and under cultural practices typical of commercial *Mandevilla* production. During the production of the plants, day temperatures averaged 25° C. and night temperatures averaged 15° C. Plants were six months old when the photographs and detailed description were taken. In the following description, color references are made to The Royal Horticultural Society Colour Chart, 2007 Edition, except where general terms of ordinary dictionary significance are used.

Botanical classification: *Mandevilla hybrida* 'Sunpa 127'.

Parentage:

*Female, or seed, parent*.—Proprietary selection of *Mandevilla hybrida* identified as code number 02MH11-4, not patented.

*Male, or pollen, parent*.—Proprietary selection of *Mandevilla hybrida* identified as code number MH-58, not patented.

Propagation:

*Type*.—By terminal vegetative cuttings.

*Time to initiate roots, summer and winter*.—About two weeks at temperatures about 23° C. to 25° C.

*Time to produce a rooted young plant, summer and winter*.—About five to six weeks at temperatures about 23° C. to 25° C.

*Root description*.—Fibrous; typically light brown in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Trailing plant habit; vigorous growth habit; freely branching habit.

*Lateral branch description*.—Length: About 19 cm. Diameter: About 2.8 mm. Internode length: About 1.8 cm. Strength: Strong, flexible. Texture: Smooth, glabrous. Color, developing: Close to 144B. Color, fully developed: Close to 177C.

Leaf description:

*Arrangement*.—Opposite, simple.

*Length*.—About 4.9 cm.

*Width*.—About 3.8 cm.

*Shape*.—Elliptic.

*Apex*.—Acuminate.

*Base*.—Cordate.

*Margin*.—Entire.

*Texture and luster, upper and lower surfaces*.—Smooth, glabrous; slightly glossy.

*Venation pattern*.—Pinnate, reticulate.

*Color*.—Developing leaves, upper surface: Close to 146A. Developing leaves, lower surface: Close to 147C. Fully expanded leaves, upper surface: Close to NN137B; venation, close to 145B. Fully expanded leaves, lower surface: Close to 147B; venation, close to 145C.

*Petioles*.—Length: About 1.2 cm. Diameter: About 1.2 mm. Texture, upper and lower surfaces: Smooth, glabrous. Color, upper and lower surfaces: Close to N144A slightly tinged with close to 179B.

Flower description:

*Flower type and habit*.—Single salverform flowers arranged in axillary racemes; flowers face mostly outwardly; freely flowering habit with about two to three flowers per inflorescence and about 50 flowers developing per plant.

*Natural flowering season*.—Early flowering habit, plants begin flowering about six weeks after planting; long flowering period, plants flower continuously from early summer until late autumn in Japan.

*Flower longevity on the plant*.—About seven to ten days; flowers not persistent.

*Fragrance*.—None detected.

*Flower buds*.—Height: About 6.4 cm. Diameter: About 1.2 cm. Shape: Rhomboid. Color: Distally, close to 38B; mid-section, close to 145C; proximally, close to 145B tinged with close to 180B.

*Flowers*.—Appearance: Salverform; flared trumpet, corolla fused and five-parted; flowers roughly star-shaped. Diameter: About 6 cm. Depth (length): About 5.9 cm. Throat diameter: About 1.6 cm. Tube length: About 2.4 cm. Tube diameter, proximally: About 3.1 mm.

*Corolla*.—Quantity and arrangement: Five petals arranged in a single whorl and fused towards the base into an elongated tube; petal lobes not to very slightly imbricate. Petal lobe length: About 2.9 cm. Petal lobe width: About 2.5 cm. Petal lobe shape: Ovate, asymmetrical. Petal lobe apex: Acuminate. Petal lobe margin: Entire; slightly undulate; moderately recurved. Petal lobe texture and luster, upper and lower surfaces: Smooth, glabrous; velvety; matte. Throat texture: Smooth, glabrous. Tube texture: Smooth, glabrous. Color: Petal lobe, when opening and fully opened, upper surface: Close to NN155C; at the margin, close to 70C; venation, close to NN155C; color does not change with development. Petal lobe, when opening and fully opened, lower surface: Close to NN155C; at the margins, close to 70C; venation, close to NN155C; color does not change with development. Throat: Close to 21B; proximally, close to 21A; venation, similar to lamina colors. Tube: Close to N155C; proximally, close to N155B.

*Calyx*.—Quantity and arrangement: Five sepals arranged in a single whorl, fused at the base; calyx, star-shaped. Sepal length: About 6.9 mm. Sepal width: About 2.7 mm. Sepal shape: Lanceolate. Sepal apex: Acuminate. Sepal margin: Entire. Sepal texture, upper and lower surfaces: Smooth, glabrous. Sepal color, upper surface: Close to 39A; proximally, close to 145A. Sepal color, lower surface: Close to 39A; proximally, close to 145B.

*Peduncles*.—Length: About 2.5 cm. Diameter: About 1.8 mm. Texture: Smooth, glabrous. Aspect: Upright to outwardly. Color: Close to 144A.

*Pedicels*.—Length: About 1.4 cm. Diameter: About 1.9 mm. Texture: Smooth, glabrous. Aspect: Upright to outwardly. Color: Close to 153A slightly overlain with close to 176C.

*Reproductive organs*.—Stamens: Quantity and arrangement: Typically five; filaments fused to corolla; anthers, connivent. Anther size: About 1.3 mm by 10 mm. Anther shape: Lanceolate. Anther color: Close to 16B. Pollen amount: None observed. Pistils: Quantity: Typically one. Pistil length: About 3 cm. Style color: Close to 144D. Stigma shape: Globose. Stigma color: Close to 144B. Ovary color: Close to 144B.

*Seeds and fruits*.—To date, seed and fruit production have not been observed on plants of the new *Mandevilla*.

Pathogen & pest resistance: To date, plants of the new *Mandevilla* have not been noted to be resistant to pathogens and pests common to *Mandevilla* plants.

Garden performance: Plants of the new *Mandevilla* have been observed to tolerate wind, rain and temperatures ranging from about 4° C. to about 30° C.

It is claimed:

1. A new and distinct *Mandevilla* plant named 'Sunpa 127' as illustrated and described.

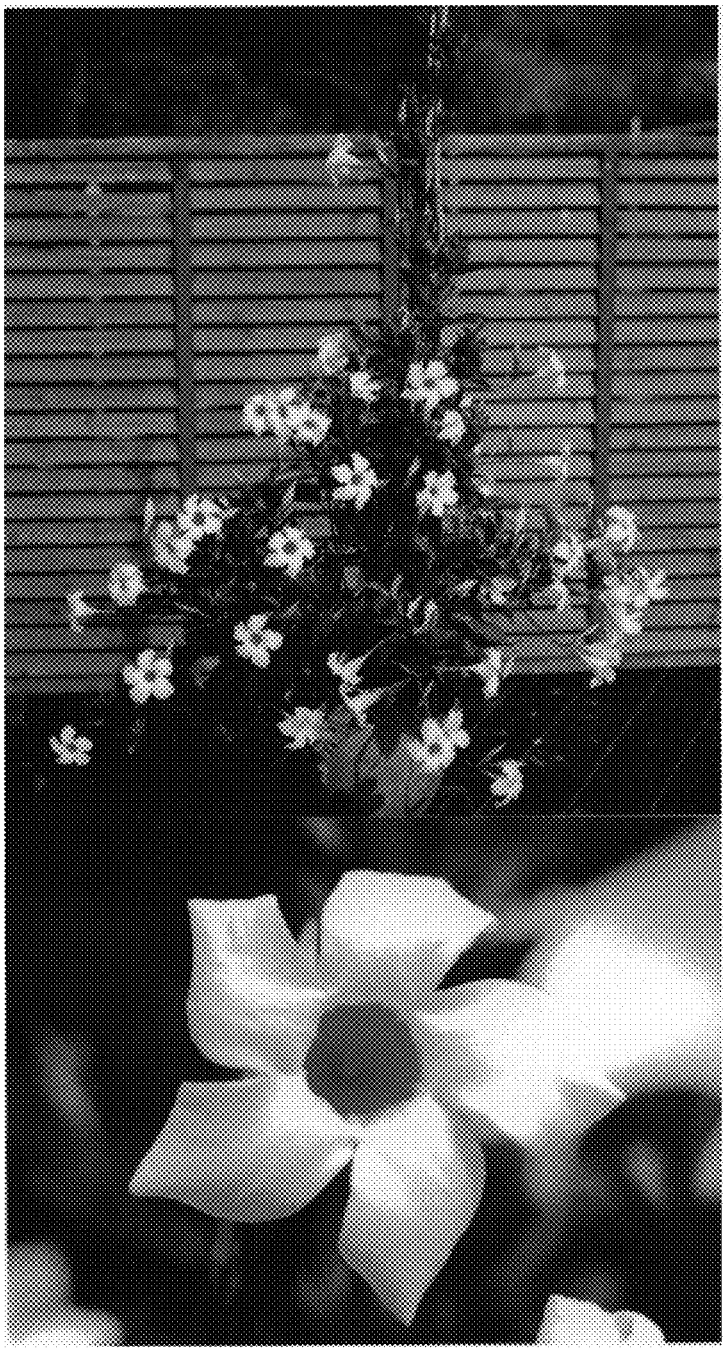

* * * * *